United States Patent [19]
Alario et al.

[11] Patent Number: 5,288,935
[45] Date of Patent: Feb. 22, 1994

[54] METHOD OF PRODUCING LIQUID HYDROCARBONS FROM NATURAL GAS, IN THE PRESENCE OF A CATALYST BASED ON ZEOLITE AND GALLIUM

[75] Inventors: Fabio Alario, La Varenne; Charles Cameron; Jean-Francois Joly, both of Paris, all of France

[73] Assignee: Institut Francais du Petrole, Rueil Malmaison, France

[21] Appl. No.: 886,226

[22] Filed: May 21, 1992

[30] Foreign Application Priority Data

May 21, 1991 [FR] France .................. 91 06195

[51] Int. Cl.$^5$ .............................................. C07C 2/78
[52] U.S. Cl. .................... 585/322; 585/417; 585/418; 585/500; 585/658; 585/700
[58] Field of Search ............... 585/322, 407, 408, 415, 585/417, 418, 943, 500, 700, 658

[56] References Cited

U.S. PATENT DOCUMENTS

| | | | |
|---|---|---|---|
| 4,304,657 | 12/1981 | Miller | 585/415 |
| 4,350,835 | 9/1982 | Chester et al. | 585/419 |
| 4,582,949 | 4/1986 | Kieffer | 585/322 |
| 4,754,091 | 6/1988 | Jezl et al. | 585/322 |
| 4,766,264 | 8/1988 | Bennett et al. | 585/418 |
| 4,806,701 | 2/1989 | Shum | 585/419 |
| 4,855,522 | 8/1989 | Diaz | 585/418 |
| 4,990,715 | 2/1991 | Knox | 585/418 |
| 5,025,108 | 6/1991 | Cameron et al. | 585/500 |
| 5,026,921 | 6/1991 | Degnan, Jr. et al. | 585/418 |

OTHER PUBLICATIONS

Patent Abstracts of Japan, vol. 12, No. 181, 27 Mai 1988 & JP-A-62 285 987 (Research Association Utilisation of Light Oil) 11 Dec. 1987.

Primary Examiner—Anthony McFarlane
Attorney, Agent, or Firm—Millen, White, Zelano, & Branigan

[57] ABSTRACT

The invention concerns a method of producing liquid hydrocarbons from natural gas, characterized in that:
a) the natural gas is separated in (2) into at least two fractions, a first fraction of gas enriched with methane and a second fraction enriched with C2+ alkanes
b) the methane is selectively oxidised in (7a) by molecular oxygen in the presence of a catalyst for oxidizing linkage of methane
c) the fraction enriched with C2+ alkanes is at least partly mixed with the effluent from selective oxidation, when at least 80% of the molecular oxygen introduced at stage (b) has already been consumed at stage (b)
d) the mixture resulting from stage (c) is pyrolysed in (7b)
e) when the temperature of the mixture from stage (d) has been brought to a temperature from 300° to 750° C. and more particularly from 420° to 550° C., at least part of the olefins is converted to aromatics in (11c), in the presence of a special catalyst containing a zeolite, gallium, one or more Group VIII metals and/or rhenium, one or more additional metals selected from tin, lead, indium, germanium and thallium, possibly an alkali metal or alkaline earth metal and possibly a matrix.

18 Claims, 1 Drawing Sheet

METHOD OF PRODUCING LIQUID HYDROCARBONS FROM NATURAL GAS, IN THE PRESENCE OF A CATALYST BASED ON ZEOLITE AND GALLIUM

FIELD OF THE INVENTION

The invention concerns a method of producing liquid hydrocarbons from natural gas. More specifically, it concerns the conversion of natural gas, the main constituent of which is methane, to liquid products which can be transported more easily. The invention concerns a method characterised in that:

SUMMARY OF THE INVENTION (a) natural gas is separated into at least two fractions, a first fraction of gas enriched with methane and a second fraction enriched with C2+ alkanes (ethane, propane and higher alkanes);

(b) at least part of the methane is oxidised selectively by molecular oxygen in the presence of a catalyst for oxidising linkage of methane (c) at least part of the fraction enriched with C2+ alkanes is mixed with the effluent from the selective oxidation stage, when at least 80% of the molecular oxygen introduced at stage (b) has been consumed at stage (b);

(d) the mixture resulting from stage (c) is pyrolysed;

(e) when the temperature of the mixture from stage (d) has been brought to 300° to 750° C. and more particularly 420° to 550° C., at least part of the olefins and possibly part of the C2+ alkanes are converted to aromatics in the presence of a particular catalyst, containing a zeolite, gallium, one or more Group VIII metals and/or rhenium, one or more additional metals selected from tin, lead, indium, germanium and thallium, possibly an alkali metal or alkaline earth metal and possibly a matrix.

The composition of the catalyst will be explained below.

The basic principles of the method of oxypyrolysis of natural gas, combining selective oxidation of methane and pyrolysis of the C2+ alkanes which are formed and added to the oxidation effluent, are described in three French Patents (2 629 451, 2 636 627 and 2 641 531) and an article (Appl. Catal., vol. 58 (1990) 269).

At a first stage, stage (a) of the process, natural gas is separated into at least two fractions, the first being methane with a reduced quantity of C2+ alkanes (ethane, propane and higher alkanes) and the second fraction being made up of C2+ higher alkanes with a reduced quantity of methane. At least part of the first fraction is then mixed with oxygen (pure or enriched) up to 0.4 mol of molecular oxygen per mol of carbon. The mixture may advantageously contain large quantities of water vapour. The molar quantity of water vapour relative to methane may be from 0 to 4, preferably from 0 to 2, still more preferably from 0 to 1 and more particularly from 0.05 to 0.50. The water vapour makes oxygen/hydrocarbon mixtures easier to handle and permits a simultaneous increase in selectivity for products of linkage and conversion of methane at the selective oxidation of methane stage.

The second stage, stage (b) of the process, comprises consuming the molecular oxygen in a selective catalytic oxidation reaction at temperatures at least above 650° C., preferably above 750° C. and still more preferably above 800° C. The pressure is generally from 1 to 15 bars, preferably from 1 to 10 bars and more particularly from 1 to 4 bars. The reaction, generally described as oxidising linkage of methane, is carried out in the presence of a catalyst which is stable at high temperature. Catalysts which are stable at high temperature are generally those containing at least one refractory oxide such as magnesia, calcium oxide, strontium oxide and the other oxides contained in Table 3 of the article which appeared in Appl. Catal., vol. 67 (1990) 47. Catalysts which are of particular interest for oxidising linkage of methane are inter alia those described in French patent 2 629 451 and the articles published in Appl. Catal., vol. 67 (1990) 47 and Chem. Soc. Rev., vol. 18 (1989) 251.

The selective oxidation stage may be carried out in a fixed bed reactor, a moving bed reactor or a conveyed bed reactor. Use of a fixed bed reactor is particularly advantageous in cases where the catalyst does not have good mechanical strength properties and for a relatively low methane conversion per operation, e.g. less than 20%. Moving bed reactors, such as those with a boiling bed or a conveyed bed, are very advantageous when the conversion per operation is e.g. over 20%. Circulation of the catalyst gives better temperature control through heat exchange between the charge, the catalyst and the effluents.

Whichever reactor is used for the selective oxidation of methane stage, that stage is highly exothermic. It is therefore very important to lower the temperature of the effluent in order to limit the formation of acetylene and coke, which may form during the long times of contact at high temperature. For this reason it is often advantageous to inject at least part of the second fraction into the hot effluent, the second fraction comprising higher C2+ alkanes with a reduced quantity of methane, emanating from the first stage. C2+ hydrocarbons, which are generally paraffinic, serve to lower the temperature by carrying out thermochemical quenching; in other words they absorb the heat liberated by the oxidation stage and are converted to olefins and hydrogen.

The third stage, stage (c), comprises adding at least part of the C2+ paraffins obtained at stage (a) to the effluent from selective oxidation of methane when at least 80% and preferably at least 95% of the molecular oxygen introduced at stage (b) has already been consumed at the second stage. This mode of operation has three advantages:

1. at stage (b), selective oxidation of methane, it is not necessary to operate in the presence of C2+ hydrocarbons which are more oxidisable than methane;

2. the addition of C2+ hydrocarbons in the effluent from selective oxidation of methane, after at least 80% and preferably at least 95% of the molecular oxygen introduced at stage (b) has already been consumed, enables most of the molecular oxygen to be used to activate methane rather than to dehydrogenate C2+ alkanes;

3. the addition of C2+ hydrocarbons in the effluent from selective oxidation of methane, after at least 80% and preferably at least 95% of the molecular oxygen introduced at stage (b) has already been consumed, enables C2+ alkanes to be converted by heat absorption to olefins and hydrogen; the latter may be used to recover carbon, e.g. by hydrogenating CO to methane.

The fourth stage, stage (d) comprises maintaining the dwell time of the combined effluents for a long enough time to enable an ethylene/ethane molar ratio of at least 1.2 and preferably over 1.4:1 preferably to be obtained. During this stage the dwell time is generally from 50 milliseconds to 10 seconds, preferably from 100 milliseconds to 2 seconds.

In a method of producing liquid hydrocarbons from natural gas which does not form part of this invention, the gaseous effluent leaving the fourth stage, stage (d), is brought to a temperature below 100° C., compressed and put into the separating system. The compressed gas is then freed from water and CO2 before the higher hydrocarbons (C2, C2=, C3, C3= and higher hydrocarbons) are separated from the light gases (CO, H2, CH4). The higher hydrocarbons are then:

1. separated to produce olefins (ethylene, propylene and higher olefins) and recyclable alkanes,
2. oligomerised and/or aromatised to obtain liquid hydrocarbons and recyclable alkanes, or
3. dimerised to produce liquid C4+ olefins and recyclable alkanes.

In the method of the invention the effluent from oxypyrolysis, in the gas state and containing gases including hydrocarbons such as ethylene, ethane and propylene, is advantageously treated on an aromatising catalyst. It is indeed of great interest to upgrade these C2-C3 hydrocarbons to liquids such as major petrochemical products.

The effluent from stage (d), which is then used for the stage (e) charge, comprises:

1. at least 40% and no more than 95% by weight of the methane plus water;
2. at least 5%, preferably at least 10% and still more preferably at least 15% by weight of non-paraffinic hydrocarbon compounds;
3. less than 1%, preferably less than 0.5% and still more preferably less than 0.1% by weight of molecular oxygen; and
4. other compounds (in quantities which vary depending on the initial charge at stage (a) and operating conditions at stages (a) to (d)), such as N2, CO, CO2, H2 and C2+ alkanes.

The fifth stage, stage (e). thus comprises bringing the effluent from stage (d) to a temperature from 300° to 750° C. and more particularly from 420° to 550° C., then putting the effluent into contact with a particular aromatising catalyst which enables at least part of the olefins to be converted to liquid hydrocarbons. Conversion of the olefins and possibly at least part of the C2+ alkanes to liquid hydrocarbons may have important effects on the dimensions of the separating system. Furthermore the grouping of a hot unit such as the aromatising unit with other hot units before the cold separating stages has positive effects on the investment required for the operating unit for upgrading natural gas.

The invention has two important advantages. The at least partial conversion of the olefins and possibly the C2+ alkanes to aromatics before they enter the separating system makes it possible:

1. to reduce the dimensions of the separating system
2. to reduce the services called for, by bringing together a hot (aromatisation) unit with other hot (oxidation and pyrolysis) units.

Figure 1:
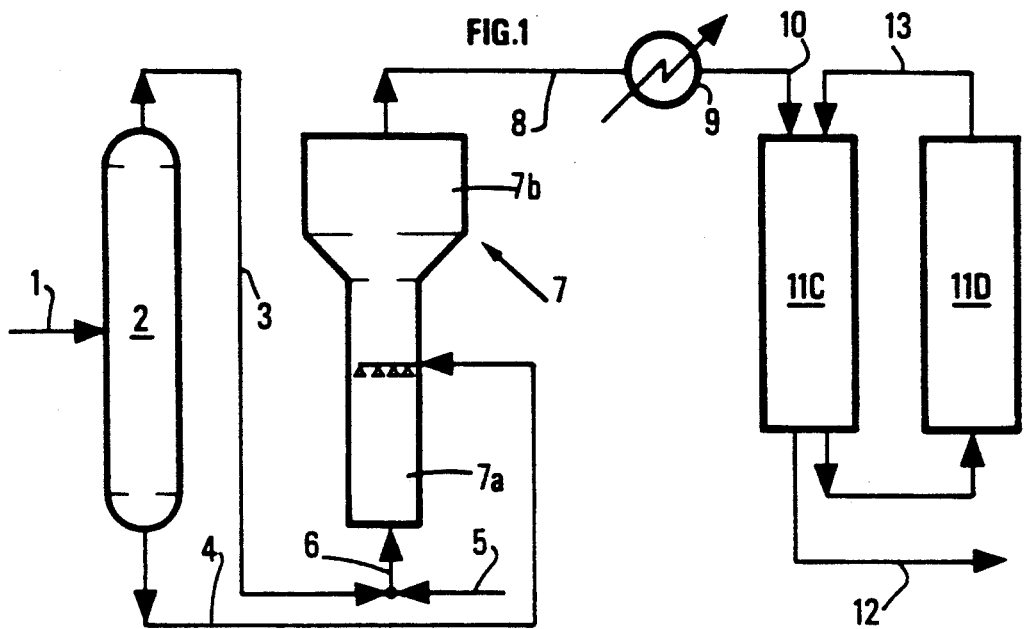
FIGS. 1 and 2 are schematic embodiments of the invention, FIG. 1 relating to a vertical reactor and FIG. 2 relating to a horizontal reactor.

A preferred embodiment of the invention comprises using a fluidized bed reactor for the selective oxidation and pyrolysis (oxypyrolysis) stages and a reactor of the moving bed type for aromatisation. In this embodiment the gas enriched with methane (3), emanating from separation of natural gas (1) in the separator (2), is mixed with molecular oxygen (5). In cases where it is advantageous to add water vapour to the charge, this is generally added either to the methane or to the oxygen, or to the methane and oxygen before the methane is mixed with the oxygen. It is very important to control the temperature of the gaseous mixture before it enters the reactor. For this purpose the gases containing methane (3) and the oxygen (5) may be heated independently or the gases (6) together. When the gases have been preheated to a temperature generally below 750° C. and preferably below 600° C. they are put into contact with the catalyst for oxidising coupling of methane in the lower part (7a) of the reactor (7) in FIG. 1 or in the upstream part (7a) of the reactor (7) in FIG. 2.

The catalyst for this type of application must have good mechanical strength. The particles are generally from 20 microns to 4 mm in diameter. The size of the catalyst particles varies according to the operating conditions of the unit and the density of the catalyst. Although it is not possible to name all the catalysts for oxidising coupling of methane which are potentially of interest for an application in a boiling bed reactor, mention may be made of catalysts described in French patent 2 629 451, in Appl. Catal., vol. 76 (1990) 47, in Chem. Soc. Rev., vol. 18 (1989) 251 and, for example, catalysts such as: BaCO3/Al2O3 (generally though not necessarily in the presence of a few ppm of a chlorine source in the charge); Pb/Al2O3 (often in the Presence of an alkali metal and/or an anion containing sulphur or phosphorus); mixed oxides containing Na, B, Mg and Mn (such as NaB2Mg4Mn20x; La/MgO (often in the presence of one or more alkaline earth metal or alkali metal oxides and/or other lanthanide oxides and possibly boron); Na or K combinations, one or more alkaline earth metal oxides and possibly boron; MCeO3 perovskites (where M=Sr or Ba) and mixed oxides containing thorium or yttrium.

After undergoing selective oxidation in the reactor (7) and at a location where at least 80% of the molecular oxygen introduced at stage (b) has been consumed, at least part of the gas fraction enriched with C2+ alkanes (4) is added in the reactor. This fraction may be added in the expanded bed of catalyst (FIG. 1) or at a level above the catalyst (such as the liberation zone).

After a long enough dwell time in the reactor (stage (d) of the process) to obtain the desired olefin content, the gases are passed along the line (8) to a heat exchanger (9), where their temperature is lowered to 300° to 750° C. and more particularly 420° to 550° C. The effluent is then passed through the line (10) in FIG. 1 to the aromatising reactor (11c). If the operating pressure of the aromatising reactor (11c) is above the pressure in the line (10), the effluent may advantageously be compressed at that point in time.

Figure 2:
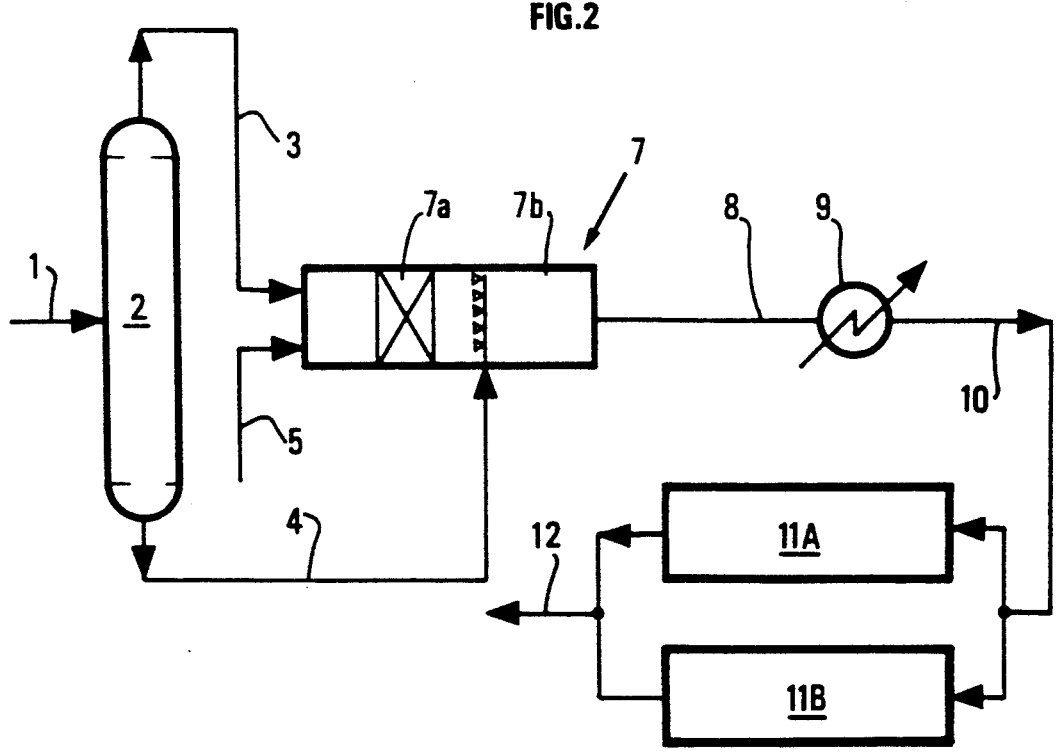

In one of the preferred embodiments the aromatising reactor (11c) in FIG. 1 receives the charge to be aromatised with fresh catalyst through its upper part. In this way the catalyst deactivated by coking is removed at the bottom of the reactor. The deactivated catalyst is then regenerated at (11d) before being fed back through the line (13) into the upper part of the reactor. The charge entering the reactor is put into contact with an aromatising catalyst, which is defined as follows in this invention:

The catalyst will contain:
1. a zeolite,
2. gallium,
3. at least one metal from the group made up of Group VIII metals and rhenium,
4. at least one additional metal
5. possibly at least one alkali metal or alkaline earth metal and,
6. possibly at least one matrix.

The composite catalyst preferably contains an MFI zeolite in hydrogen form, possibly gallium in its crystallised framework, gallium in oxide form and a generally amorphous matrix. At least one Group VIII metal, preferably a metal of the platinum family: Ru, Rh, Pd, Os, Ir and Pt and/or rhenium, at least one additional metal selected from the group made up of tin, germanium, lead, indium, gallium and thallium, or from metals such as copper, gold, silver or from Group VI metals such as chromium, molybdenum or tungsten are deposited on the matrix, and the matrix may possibly contain at least one alkali metal or alkaline earth metal (preferably lithium or potassium).

The MFI zeolite contained in the catalyst of the invention may be prepared by any of the methods described in prior art. Thus it may be synthesised in a conventional OH medium in the presence or absence of organic agent and/or alcohol. The document "Synthesis of High Silica Zeolites, P.Jacobs and J.Martens, Studies in Surface Science and Catalysis, vol.33 (1987)" describes conventional synthesis of MFI zeolite. The MFI zeolite used in the invention may equally have been synthesised in less conventional media, for example in the fluoride medium, either in the presence of organic compound (patent EP-A-172068) or in its absence (French patent application 90/16529). The zeolite used in the invention contains the elements silicon, aluminium and/or gallium in its crystallised framework.

After the synthesising stage the MFI zeolite is converted to a hydrogen form, written H-MFI, by eliminating virtually all the organic compounds and/or alkali metal or alkaline earth metal cations which it may possibly contain after synthesis. Any of the methods described in prior art may be used for the passage to the hydrogen form, such as ion exchanges, which may or may not be followed by calcination, and various chemical treatments.

Any of the zeolites synthesised in one of the following systems: Si-Al, Si-Al-Ga, Si-Ga are suitable for the invention. However their Si/T ratio, where T represents Al and/or Ga, is generally over 7:1, preferably over 25:1 and still more preferably from 40 to 500:1.

The H-MFI zeolite used in the invention may have gallium deposited on it in its existing state. Alternatively it may be mixed with the other constituents of the catalyst, with the gallium subsequently being included in the mixture.

Many methods of depositing gallium may be used in the invention, including the following:
  ion exchange using gallium salts in aqueous solution, e.g. gallium nitrate, chloride or hydroxide
  impregnation with solutions of said gallium salts.

The quantity of gallium deposited on the composite catalyst is from 0.01 to 10% by weight, preferably from 0.03 to 7%.

The matrix includes at least one refractory oxide, particularly at least one oxide of a metal selected from the group comprising magnesium, aluminium, titanium, zirconium, thorium, silicon and boron. It may additionally include charcoal.

The preferred matrix is alumina, and its specific surface area may advantageously be from 10 to 600 m2/g, preferably 150 to 400 m2/g.

The composite catalyst of the invention may be prepared by two methods which are described theoretically below; their practical execution is known to persons skilled in the art.

First Method

The H-MFI zeolite is mixed with the matrix. The mixture may be made from two powders, two solids which have previously been shaped separately, or a powder and a solid which has previously been shaped separately. The two solids may alternatively be shaped together by any of the methods described in prior art: pelleting, extrusion, tabletting, oil dropping or spray drying. During these shaping operations a shaping additive may be included if necessary, selected from the group comprising silica and alumina. Thus the procedure of mixing the zeolite with the matrix and/or shaping them either separately or together is carried out. After the mixing and/or shaping step the metals and gallium are deposited on the entity comprising the matrix and the zeolite, the depositing order being unimportant. The majority of the metal, i.e. 30 to 100% by weight and preferably 60 to 100% relative to the composite catalyst, is then considered to be on the matrix. The gallium is either on the matrix or extremely close to the acid sites of the H-MFI zeolite.

Second Method

In a preliminary step the metals are deposited on the matrix and the gallium on the H-MFI zeolite. The H-MFI zeolite containing gallium is then mixed with the matrix containing the metals, and they are shaped either separately or together; shaping is obtained under the same conditions as previously. In a different form of the method, the zeolite with the gallium deposited on it may be mixed with the matrix at any stage in the deposition of metals on the matrix.

The preferred method of preparation is to deposit the gallium on the zeolite, to deposit the metals on the matrix, then to incorporate the zeolite charged with gallium in the matrix charged with metals by shaping the two powders. Shaping is preferably carried out after micronic grinding, which may be done by the wet grinding method.

The composite catalyst contains from 1 to 99% by weight of zeolite, the balance to 100% consisting of the matrix, metals and gallium. The respective proportion of zeolite and matrix varies widely, since it depends firstly on the Si/T ratio of the zeolite, where T is Al and/or Ga, and secondly on the metal content of the matrix in the case of the preferred method of preparation.

In the preferred method of preparation the matrix containing the metals is generally prepared by a procedure described below.

The material used to impregnate the metals is either a combined solution of the metals which are to be introduced, or separate solutions for the Group VIII metal or metals and/or rhenium and for the additional metal or metals selected from tin, lead, indium, germanium and thallium and possibly the element selected from the group comprising alkali metals and alkaline earth metals. When a plurality of solutions are used, intermediate drying and/or calcining operations may be carried out. The procedure normally ends with calcination, e.g. at 500° to 1 000° C., preferably in the presence of molecular oxygen, e.g. by scavenging with air.

The Group VIII metal or metals and/or rhenium may be incorporated in the matrix by impregnating the matrix with an aqueous or non-aqueous solution containing a salt or compound of Group VIII and/or rhenium. Platinum is generally incorporated in the matrix in the form of chloroplatinic acid, but for any noble metal it is also possible to use ammoniated compounds or compounds such as ammonium chloroplatinate, dicarbonyl platinum dichloride, hexahydroxyplatinic acid, palladium chloride or palladium nitrate.

The additional metal selected from the group comprising tin, germanium, lead, indium, gallium and thallium, or from metals such as copper, gold, silver, nickel, iron, or from Group VI metals such as chromium, molybdenum or tungsten may be introduced by means of compounds such as tin chlorides, bromides and nitrates, lead halides, nitrate, acetate and carbonate, germanium chloride and oxalate or indium nitrate and chloride. The element selected from the group comprising alkali metals and alkaline earth metals, preferably lithium or potassium, may be introduced by means of compounds such as the halide, nitrate, carbonate, cyanide and oxalate of the said element.

The use of at least one Group VIII metal or rhenium may, for example, take place by using ammoniated compounds.

In the case of platinum mention may be made e.g. of platinum IV salts which are hexamines of the formula $Pt(NH_3)_6X_4$; halopentamines of the formula $(PtX(NH_3)_5)X_3$; tetrahalodiamines of the formula $PtX_4(NH_3)_2$; platinum complexes with halogen-polyketones and halogenated compounds of the formula $H(Pt(acac)_2X)$; X being a halogen selected from the group formed by chlorine, fluorine, bromine and iodine, and of reference X being of chlorine, and acac representing the formula $C_5H_7O_2$ radical derived from acetylacetone.

The Group VIII metal or rhenium is preferably introduced by impregnation with an aqueous or organic solution of one of the above-mentioned organometallic compounds. Organic solvents which may be employed include paraffinic, naphthenic or aromatic hydrocarbons and halogenated organic compounds with e.g. from 1 to 12 carbon atoms per molecule. Some examples are n-heptane, methylcyclohexane, toluene and chloroform. Mixtures of solvents may also be used.

When the Group VIII metal or rhenium has been introduced, the product obtained may possibly be dried, and is then calcined preferably at a temperature from 400° to 1 000° C.

After the calcination at least one additional metal may be introduced, possibly preceded by reduction with hydrogen at high temperature, e.g. from 300° to 500° C. The additional metal M may be introduced in the form of at least one organic compound selected from the group comprising complexes of said metal, particularly polyketone complexes of the metal M and hydrocarbyl metals such as metal alkyls, cycloalkyls, aryls, alkylaryls and arylalkyls.

The metal M is advantageously introduced by means of a solution of the organometallic compound of said metal in an organic solvent. Organohalogenated compounds of the metal M may equally be employed. Some special examples of compounds of the metal M are tetrabutyl tin in cases where M is tin, tetraethyl lead in cases where M is lead and triphenylindium in cases where M is indium.

The impregnating solvent is selected from the group comprising paraffinic, naphthenic or aromatic hydrocarbons containing 6 to 12 carbon atoms per molecule and halogenated organic compounds containing 1 to 12 carbon atoms per molecule. Some examples which can be mentioned are n-heptane, methylcyclohexane and chloroform. Mixtures of the solvents defined above may also be used.

In cases where the preparation process as described above is not used, one may consider incorporating at least one additional metal M before the introduction of at least one Group VIII metal or rhenium. If the metal M is introduced before the Group VIII metal or rhenium, the metal M compound used is generally selected from the group comprising the halide, nitrate, acetate, tartrate, carbonate and oxalate of the metal M. It is then advantageously introduced in aqueous solution. In this case calcination in air is carried out at a temperature from 400° to 1 000° C. before at least one noble metal is introduced.

The composite catalyst contains:
1. By weight relative to the matrix:
   0.01 to 2% and preferably 0.1 to 0.5% of at least one Group VIII metal or rhenium
   0.005 to 2% of tin and preferably 0.01 to 0.5% of tin or 0.005 to 0.7% and preferably 0.01 to 0.6% of at least one metal selected from the group comprising germanium, indium, lead, gallium and thallium, or from metals such as copper, gold, silver, nickel and iron, or from Group VI metals such as chromium, molybdenum or tungsten, the total content of metals from the group comprising tin, germanium, indium and lead being from 0.02 to 1.20%, preferably 0.02 to 1.0% and still more preferably 0.03 to 0.80%
   possibly 0.01 to 4%, preferably 0.1 to 0.6% of at least one metal selected from the group comprising alkali metals and alkaline earth metals, and preferably from the group comprising lithium and potassium.
2. from 1 to 99% by weight of MFI zeolite in hydrogen form
3. from 0.01 to 10%, preferably 0.03 to 7% by weight of gallium.

At the end of the preparation process the shaped catalyst contains an H-MFI zeolite, gallium, metals and a matrix, and calcination is carried out in air at a temperature from 450° to 1 000° C. The catalyst thus calcined may advantageously undergo activation treatment in hydrogen at high temperature, e.g. from 300° to 500° C., in order to obtain a more active metal phase and at least part of the more widely dispersed gallium oxide phase located extremely close to the acid sites of the H-MFI zeolite. The procedure for hydrogen treatment may e.g. comprise slowly raising the temperature in a stream of hydrogen to the maximum reducing temperature, generally from 300° to 500° C. and preferably from 350° to 450° C., then maintaining that temperature for a period generally of 1 to 6 hours.

The catalyst obtained by the above procedures, which may possibly undergo calcination treatment in air at a temperature generally from 350° to 690° C., is used for the reaction in which the oxypyrolysis gases are aromatised. This reaction is of particular interest as it enables hydrocarbon gases to be upgraded to liquids with a higher added value (chiefly benzene, toluene and xylenes).

The charge, which is the oxypyrolysis effluent and contains ethylene and/or ethane and/or propylene among other compounds, is put into contact with the aromatising catalyst described above, at a temperature from 300° to 750° C. and more particularly from 420° to 550° C., with an hourly throughput of charge by mass relative to the weight of catalyst (PPH) from 0.5 to 150 $h^{-1}$, preferably from 1 to 80 $h^{-1}$. The operating pressure will advantageously be from 1 to 18 bars, preferably from 1 to 12 bars.

The effluent from said aromatising reactor (11c), enriched with aromatics, is transferred through the pipe (12) to the separating system.

Another preferred embodiment of the invention comprises using a fixed bed reactor (7) for the selective oxidation and pyrolysis stages, preferably but not necessarily in the same chamber (there are thus two separate zones 7a and 7b here). In a special method (cf FIG. 2) aromatisation may take place in at least one reactor referred to as (11a) and (11b), which can be taken "out of circuit" to regenerate the catalyst contained in it (a swing reactor). In this embodiment of the invention the catalysts used for selective oxidation of methane and aromatisation of at least part of the olefins and possibly part of the C2+ alkanes need not necessarily be very wear resistant. So the catalyst may appropriately be used in the form of extrusions, fragments or particles. All catalysts previously mentioned for an application in a fluidized bed reactor may be used for an application in a fixed bed reactor. The catalyst for this type of embodiment need not necessarily have particularly high mechanical strength.

In cases where it is advantageous to add water vapour to the charge, it is generally added either to the methane or to the oxygen, or to the methane and oxygen before the methane is mixed with the oxygen. It is very important to control the temperature of the mixture of gases before it enters the reactor. For this purpose, in the case of a fixed bed reactor, the gases containing methane (3) and the oxygen (5) are heated independently before the methane is mixed with the oxygen. The methane and oxygen are mixed in the chamber of the reactor (7) before coming into contact with the catalyst. Since mixing is effected in the reactor, the pipe (6) may not be necessary for this embodiment. It is nevertheless often advantageous for part of the preheating of the gases to take place in the reactor. The water present in the charge is able to receive heat liberated by the catalyst, by radiation. So part of the preheating may take place in the oxidation reactor by this method. The gases, preheated to a temperature generally below 750° C. and preferably below 600° C., are then put into contact with the catalyst for oxidising linkage of methane in the reactor (7).

After undergoing selective oxidation in the reactor (7) and at a location where at least 80% of the molecular oxygen introduced at stage (b) has been consumed, at least part of the gas fraction enriched with C2+ alkanes (4) is added in the reactor. The place where this fraction is added is generally after the catalytic bed for reasons of simple operation.

After a dwell time long enough (pyrolysis) to obtain the desired olefin content (ethylene/ethane molar ratio of at least 1.2:1), the gas is conveyed to the aromatising reactor through the lines (8) and (10) via the unit (9). The aromatising reactor unit, referred to as (11a) and (11b), operates discontinuously. The part (11a) of the reactor unit, for example, receives the gas to be aromatised at a temperature and for a time long enough to convert at least part of the olefins and possibly part of the C2+ alkanes to aromatics. For at least a period of this conversion in part (11a) of the reactor unit, part (11b) is set to regeneration, in order to remove the carbon deposited on the catalyst during the previous cycle. After the regeneration stage part (11b) is put back into service, and so on.

The aromatised effluent in the aromatising reactor is then passed to the separating system through the line (12).

The following examples specify the process but without restricting its scope.

EXAMPLE 1: Preparation of alumina containing platinum, tin and lithium (catalyst A)

100 cm3 of an aqueous solution of lithium nitrate is added to 100 g of alumina carrier. They are left in contact for 6 hours, drained, dried for 1 hour at 100°-120° C. and calcined in a stream of dry air for 2 hours at 350° C.

The calcined product containing lithium is impregnated with platinum by adding 100 cm3 of a solution of acetylacetonate in toluene to the solid. The concentration of platinum in the solution is 3 g/l. The solid and solution are left in contact for 6 hours, dried for 1 hour at 100°-120° C. then calcined for 2 hours at 530° C. The material is reduced in a stream of dry hydrogen for 2 hours at 450° C.

After reduction the product containing lithium and platinum is submerged in n-heptane with 100 g of solid per 300 cm3 of hydrocarbon solvent. 3 g of tetra-n-butyl tin solution solution in n-heptane (containing 10% by weight of tin) is then injected into the n-heptane containing the catalyst. The solid containing platinum and the tetra-n-butyl tin solution are kept in contact for 6 hours at the reflux temperature of the heptane. The impregnating solution is then removed and three washes are carried out with pure n-heptane at the reflux temperature of the n-heptane, after which the catalyst is dried. It is calcined in air for 2 hours at 500° C. then reduced in a stream of hydrogen at 450° C. before being fed into the reactor.

The alumina then contains (by weight) 0.3% of platinum, (by weight) 0.3% of tin and 0.5% of lithium.

EXAMPLE 2: MFI zeolite in hydrogen form and catalyst B containing the H-MFI zeolite and gallium An H-MFI zeolite in hydrogen form is used, supplied by CONTEKA under reference CBV 5020. The H-MFI zeolite is characterised by an Si/Al ratio of 29:1, a sodium content of 0.014% by weight and a pore volume, measured by nitrogen adsorption at 77K, of 0.192 cm3/g.

The gallium is deposited on the zeolite by ion exchange. The exchange solution is prepared from gallium nitrate GA(NO3)3 with a normality of 0.15N. The pH of the gallium nitrate solution is adjusted to a value of 2 by adding ammonia.

The gallium content obtained in the resultant catalyst B, after three successive ion exchanges between the H-MFI zeolite and the solution described above, is 3.5% by weight.

EXAMPLE 3: Conversion of an effluent from oxypyrolysis

Catalyst C, obtained after pelleting an equal-mass mixture of catalyst A from Example 1 and catalyst B from Example 2, is used to aromatise an effluent from oxypyrolysis, the composition of which (by weight) is given in Table 1. The oxypyrolysis effluent (10) will be described in the following as the "charge" and its products of conversion on the aromatising catalyst as "products".

TABLE 1

|  | Charge % (wt) |
|---|---|
| $C_1$ | 55.7 |
| $C_2=$ | 15.0 |
| $C_2$ | 2.51 |
| $C_3=$ | 0.96 |
| $H_2$ | 1.30 |
| CO | 0.93 |
| $CO_2$ | 8.40 |
| $H_2O$ | 15.2 |

The aromatising catalyst is fed into a fixed bed reactor (11) where the operating conditions ar as follows:
temperature: 500° C.
pressure: atmospheric
hourly throughput of liquid charge equal to 30 times the weight of catalyst The results, in terms of percentages (by mass) of produced found in line (12), are set out in Table 2.

TABLE 2

|  | Products % (wt) |
|---|---|
| $C_1$ | 56.4 |
| $C_2=$ | 2.02 |
| $C_2$ | 2.98 |
| $C_3=$ | 0.70 |
| $C_3$ | 1.01 |
| $C_4=$ | 0.70 |
| $C_4$ | 0.79 |
| $C_5+$, non-aromatic | 0.35 |
| aromatic | 9.11 |
| $H_2$ | 1.41 |
| CO | 1.02 |
| $CO_2$ | 8.25 |
| $H_2O$ | 15.3 |

We claim:

1. In a method of producing liquid hydrocarbons from natural gas, comprising:
   (a) separating natural gas into at least two fractions, a first fraction of gas enriched with methane and a second fraction enriched with C2+ alkanes;
   (b) oxidizing at least part of the methane selectively by molecular oxygen in the presence of a catalyst by oxidizing coupling of methane;
   (c) when at least 80% of the molecular oxygen introduced at stage (b) has been consumed at stage (b), mixing at least part of the fraction enriched with C2+ alkanes from step (a) with the resultant effluent from the selective oxidation stage (b); and
   (d) pyrolyzing the mixture resulting from stage (c), the improvement which comprises:
   (e) when the temperature of the mixture from stage (d) has been brought to 300° to 750° C., and an ethylene/ethane molar ratio of at least 1.2:1 is obtained, converting at least part of the olefins and optionally part of the C2+ alkanes to aromatics in the presence of an aromatizing catalyst consisting essentially of:
   a zeolite;
   gallium;
   at least one metal selected from the group consisting of Group VIII metals of the platinum family and rhenium;
   at least one additional metal selected from the group consisting of tin, germanium, lead, indium, thallium, copper, gold, nickel, iron, chromium, molybdenum, and tungsten;
   an alkali metal or alkaline earth metal; and
   an alumina matrix.

2. The method of claim 1 wherein, during stage (e), the temperature of the mixture from stage (d) is brought to a temperature from 420° to 550° C.

3. The method of claim 1 wherein, at the end of stage (a), at least part of the first fraction (the methane fraction) is mixed with oxygen, the content of which may be up to 0.4 mol of molecular oxygen per mol of carbon.

4. The method of claim 3, wherein the mixture contains a molar quantity of water vapour of from 0 to 4 relative to the methane.

5. The method of claim 1, wherein at least part of the second fraction (C2+) obtained at stage (a) is injected into the zone for selective oxidation of methane (stage b).

6. The method of claim 1 wherein, during stage (d), the combined effluents obtained at stage (c) are maintained at a temperature of from 800° C. to 950° C., with a dwell time from 50 milliseconds to 10 seconds.

7. The method of claim 1, wherein the zeolite is an MFI.

8. The method of claim 1, wherein the catalyst contains 1 to 99% by weight of zeolite, 0.01 to 10% by weight of gallium, with the balance of 100% being formed by the carrier (matrix) charged with active agents (metals).

9. The method of claim 8, wherein the zeolite is an MFI.

10. The method of claim 3, wherein at least part of the second fraction (C2+) obtained at stage (a) is injected into the zone for selective oxidation of methane (stage b).

11. The method of claim 3 wherein, during stage (d), the combined effluents obtained at stage (c) are maintained at a temperature of from 800° C. to 950° C., with a dwell time from 50 milliseconds to 10 seconds.

12. The method of claim 5 wherein, during stage (d), the combined effluents obtained at stage (c) are maintained at a temperature of from 800° C. to 950° C., with a dwell time from 50 milliseconds to 10 seconds.

13. The method of claim 10 wherein, during stage (d), the combined effluents obtained at stage (c) are maintained at a temperature of from 800° C. to 950° C., with a dwell time from 50 milliseconds to 10 seconds.

14. The method of claim 13, wherein the aromatizing catalyst contains, by weight relative to the matrix:
   (a) 0.01% to 2% of at least one metal selected from the group consisting of Group VIII metals and rhenium, (b) 0.005% to 2% of additional metal when said additional metal is tin or 0.005% to 0.7% of additional metal when said additional metal is not tin, and (c) 0.01% to 4% of at least one alkali metal or alkaline earth metal.

15. The method of claim 1, wherein said zeolite is an MFI zeolite, said at least one metal is platinum, said at least one additional metal is tin, and said alkali metal or alkaline earth metal is lithium.

16. The method of claim 1, wherein the aromatizing catalyst is a composite of equal parts by weight of:

an alumina matrix containing by weight 0.3% platinum, 0.3% tin, and 0.5% lithium, and an H-MFI zeolite having an Si/Al ratio of 29:1, a sodium content of 0.014% by weight, and a pore volume (measured by nitrogen adsorption at 77K) of 0.192 cm$^3$/g and, deposited thereon, gallium in an amount of 3.5% by weight.

17. The method of claim 15, wherein during stage (e), the temperature of the mixture from stage (d) is brought to a temperature of 420°–550° C.

18. The method of claim 16, wherein during stage (e), the temperature of the mixture from stage (d) is brought to a temperature of 420°–550° C.

* * * * *